United States Patent
Haeusler et al.

(10) Patent No.: US 6,803,578 B2
(45) Date of Patent: Oct. 12, 2004

(54) METHOD FOR IDENTIFICATION AND PARTIAL-PRESSURE DETERMINATION OF TWO GASES IN AN UNKNOWN ANESTHESIA GAS MIXTURE

(75) Inventors: Andrea Haeusler, Lübeck (DE); Wajih Al-Soufi, Lugo (ES)

(73) Assignee: Drager Medical AG & Co. KGAA (DE)

( * ) Notice: Subject to any disclaimer, the term of this patent is extended or adjusted under 35 U.S.C. 154(b) by 157 days.

(21) Appl. No.: 10/223,464

(22) Filed: Aug. 20, 2002

(65) Prior Publication Data

US 2003/0038238 A1 Feb. 27, 2003

(30) Foreign Application Priority Data

Aug. 21, 2001 (DE) .......................................... 101 40 998

(51) Int. Cl.[7] .............................................. G01N 21/35
(52) U.S. Cl. ............................ 250/339.13; 250/339.09; 250/339.12
(58) Field of Search ................... 250/339.01, 339.06, 250/339.09, 339.12, 339.13, 340

(56) References Cited

U.S. PATENT DOCUMENTS

| | | | | |
|---|---|---|---|---|
| 4,205,913 A | * | 6/1980 | Ehrfeld et al. ................. 356/72 |
| 4,914,719 A | * | 4/1990 | Conlon et al. ......... 250/339.13 |
| 5,231,591 A | * | 7/1993 | Flewelling et al. ............ 702/24 |
| 5,731,581 A | | 3/1998 | Fischer et al. |
| 5,739,535 A | * | 4/1998 | Koch et al. ............. 250/339.13 |
| 5,920,069 A | * | 7/1999 | Fischer et al. ......... 250/339.13 |

* cited by examiner

Primary Examiner—Nikita Wells
Assistant Examiner—Christopher M. Kalivoda
(74) Attorney, Agent, or Firm—Nixon & Vanderhye PC

(57) ABSTRACT

A method for identification and partial-pressure determination of two gases in an unknown anesthesia gas mixture comprising n possible gases by measuring the infrared optical radiation, transmitted through the gas mixture, that passes through m filters having different transmission wavelength ranges, in which n is a number greater than 2 and m is a number less than n. The method evaluates the exit intensities, measured after passage through the filters, of the infrared optical radiation transmitted through the unknown gas mixture in such a way that with three filters, for instance, two gases in an unknown gas mixture comprising five possible gases can be identified, and their partial pressures can be determined. By dividing the partial pressures by the total pressure, it is optionally also possible to determine the concentration of the gases.

9 Claims, 8 Drawing Sheets

| A - B | $p_A^* = 28.09$ | $p_B^* = 11.45$ |
| --- | --- | --- |
| A - C | $p_A^* = 14.78$ | $p_C^* = 16.51$ |
| A - D | $p_A^* = 21.67$ | $p_D^* = 17.80$ |
| A - E | $p_A^* = 0.00$ | $p_E^* = 23.70$ |
| B - C | $p_B^* = 0.00$ | $p_C^* = 29.53$ |
| B - D | $p_B^* = 12.22$ | $p_D^* = 18.55$ |
| B - E | $p_B^* = 6.59$ | $p_E^* = 13.95$ |
| C - D | $p_C^* = 14.39$ | $p_D^* = 10.22$ |
| C - E | $p_C^* = 10.75$ | $p_E^* = 9.35$ |
| D - E | $p_D^* = 0.00$ | $p_E^* = 21.02$ |

Fig. 6

|  | S'1 | S'2 | S'3 |
|---|---|---|---|
| A - B | 8.18 | 6.30 | 5.96 |
| A - C | 5.97 | 6.90 | 5.46 |
| A - D | 5.06 | 6.37 | 8.72 |
| A - E | 4.57 | 6.83 | 7.31 |
| B - C | 4.96 | 8.01 | 5.65 |
| B - D | 5.08 | 6.93 | 6.06 |
| B - E | 5.61 | 6.33 | 6.22 |
| C - D | 4.80 | 7.41 | 5.96 |
| C - E | 5.22 | 6.82 | 5.83 |
| D - E | 5.37 | 6.14 | 7.17 |

Fig. 7

|  | $\|S1-S'1\|$ | $\|S2-S'2\|$ | $\|S3-S'3\|$ | $\sum_{i=1}^{3}\|Si-S'i\|$ | $\sum_{i=1}^{3}(Si-S'i)^2$ |
|---|---|---|---|---|---|
| A - B | 3.18 | 0.70 | 0.04 | 3.92 | 10.604 |
| A - C | 0.97 | 0.10 | 0.54 | 1.61 | 1.243 |
| A - D | 0.06 | 0.63 | 2.72 | 3.41 | 7.800 |
| A - E | 0.43 | 0.17 | 1.31 | 1.91 | 1.930 |
| B - C | 0.04 | 1.01 | 0.35 | 1.40 | 1.144 |
| B - D | 0.08 | 0.07 | 0.06 | 0.21 | 0.004 |
| B - E | 0.61 | 0.67 | 0.22 | 1.50 | 0.869 |
| C - D | 0.20 | 0.41 | 0.04 | 0.65 | 0.210 |
| C - E | 0.22 | 0.18 | 0.17 | 0.57 | 0.110 |
| D - E | 0.37 | 0.86 | 1.17 | 2.40 | 2.245 |

Fig. 8

METHOD FOR IDENTIFICATION AND PARTIAL-PRESSURE DETERMINATION OF TWO GASES IN AN UNKNOWN ANESTHESIA GAS MIXTURE

CROSS-REFERENCES TO RELATED APPLICATIONS

This application is based on and claims priority of German patent application No. 10140998.2-52 filed on Aug. 21, 2001, the disclosure of which is incorporated herein by reference in its entirety.

BACKGROUND AND SUMMARY OF THE INVENTION

The invention relates to a method for identification and partial-pressure determination of two gases in an unknown gas mixture comprising n possible gases, by measurement of the infrared optical radiation emitted by a radiation source and transmitted through a cuvette holding the unknown gas mixture, which radiation passes through m filters with different transmission wavelength ranges; n is a number greater than 2, and m is a number less than n.

The gas absorbs infrared optical radiation in a very specific wavelength range, and the transmission of the unabsorbed infrared optical radiation in this wavelength range is characteristic for the gas and its partial pressure.

A method for identifying and determining the concentration of at least one gas in an unknown gas mixture comprising n possible gases by measuring the infrared optical radiation transmitted through the gas mixture is described in U.S. Pat. No. 5,731,581. This uses light radiation and more than n different wavelength ranges, which strikes filters that are each permeable to these wavelength ranges. From the measured values, the at least one gas present in the unknown gas mixture is identified and its concentration determined, by multivariant statistical methods. The concentration of a gas is obtained from the quotient of the partial pressure of the gas and the total pressure. If the total pressure is known, then from the partial pressure it is always possible to learn the concentration of a gas, and vice versa.

A disadvantage of the known method is that for identifying and determining the concentration of at least one gas in an unknown gas mixture, a large number of filters and respective downstream detectors are required, specifically at least as many filters and detectors as there are possible gases in the gas mixture.

The object of the present invention is to disclose a method for identification and partial-pressure determination of two gases in an unknown gas mixture that can be performed by structurally simple means.

According to the invention, this object is attained by a method having the steps of claim 1.

The method for identification and partial-pressure determination of two gases in an unknown gas mixture comprising n possible gases by measuring the infrared optical radiation emitted by a radiation source and transmitted through a cuvette holding the unknown gas mixture, which radiation passes through m filters with different transmission wavelength ranges, in which n is a number greater than 2, and m is a number less than n, comprises the following steps.

First, either a single time or at relatively long time intervals, such as several weeks, the evaluation and control unit performs a calibration, before the actual identification and partial-pressure determination in the unknown gas mixture is performed. For each individual one of the n gases that possibly occurs in the unknown gas mixture, and for each of the m filters, which are each permeable to a special wavelength range, the exit intensity of the infrared optical radiation transmitted through the gas, once it has passed through the filter, is determined as a function of the partial pressure of the gas. This dependency can be described by means of a calibration curve. A total of n×m different calibration curves are obtained, for each of the n gases and each of the m filters.

This is followed by the identification and partial-pressure determination of two gases in an unknown gas mixture. This concept will always be understood hereinafter to include the identification and partial-pressure determination of one gas instead of two gases as well, in the event that only this one gas occurs in the unknown gas mixture. That case is a simplified special case, which will no longer be mentioned separately below but instead will be included in the concept of the identification and partial-pressure determination of two gases. For each of the m filters, the exit intensity of the infrared optical radiation transmitted through the unknown gas mixture, once it has passed through the filter, is measured by a detector downstream of the filter. The result is m values.

On the basis of an evaluation of the previously created n×m calibration curves, the evaluation and control unit for each of the possible gas mixtures, each of which comprise two of the n gases and will hereinafter be called a mixture pair, determines the particular pair of partial pressures whose associated m exit intensities best correspond to the m exit intensities measured in the unknown gas mixture, in accordance with a specified distance measure. A distance measure for determining which exit intensities, belonging to a pair of partial pressures, best correspond to the exit intensities measured in the unknown gas mixture is for example the sum of the distances between the exit intensities of one mixture pair, for a particular pair of partial pressures, and the measured exit intensities of the gas mixture, or the sum of the squares of the distances of the exit intensities of a mixture pair for a particular pair of partial pressures and the measured exit intensities of the gas mixture.

How the evaluation is done will be explained hereinafter, taking one mixture pair as an example.

Once, for each of the possible mixture pairs, the particular pair of partial pressures has been determined in which the associated exit intensities best correspond to the measured exit intensities of the unknown gas mixture in accordance with the specified distance measure, then from among the particular pairs of partial pressures, the partial pressure whose associated exit intensities best correspond to the measured exit intensities of the unknown gas mixture is ascertained. The two gases of the mixture pair that belong to this pair of partial pressures are identified as the two gases of the unknown gas mixture. Their ascertained partial pressures can optionally be used to determine the concentration, by means of division by the total pressure.

For the method, an infrared optical radiation gas measuring instrument is used that includes an infrared optical radiation source, a cuvette for the gas specimen to be measured, a plurality of optical filters with different transmission wavelength ranges, and at least one downstream detector for measuring the exit intensity of the infrared optical radiation, as well as an evaluation and control unit.

In a preferred embodiment, the method is employed for identification and partial-pressure determination of two gases in an unknown gas mixture comprising five possible gases. These can in particular be the five anesthesia gases, that is, halothane, enflurane, isoflurane, sevoflurane, and desflurane.

In a further preferred embodiment, three filters with different transmission wavelength ranges are used.

An embodiment in which four filters with different transmission wavelength ranges are used is equally possible.

The embodiments with three and four filters used are shown as examples in the drawings, and the embodiment with three filters will be described in detail below.

BRIEF DESCRIPTION OF THE DRAWINGS

FIG. 6, a table, showing the pairs of partial pressures for the ten possible gas mixture combinations, each of two different anesthesia gases, hereinafter called mixture pairs, ascertained from the calibration curves of the five different anesthesia gases;

FIG. 7, a table showing the exit intensities of the mixture pairs, the intensities being calculated on the basis of the pairs of partial pressures, ascertained in FIG. 6, of the individual anesthesia gases;

FIG. 8, a table showing the deviations of the various calculated exit intensities of the mixture pairs from the measured exit intensities of the unknown gas mixture.

DESCRIPTION OF THE EXEMPLARY EMBODIMENTS

Figure 1:
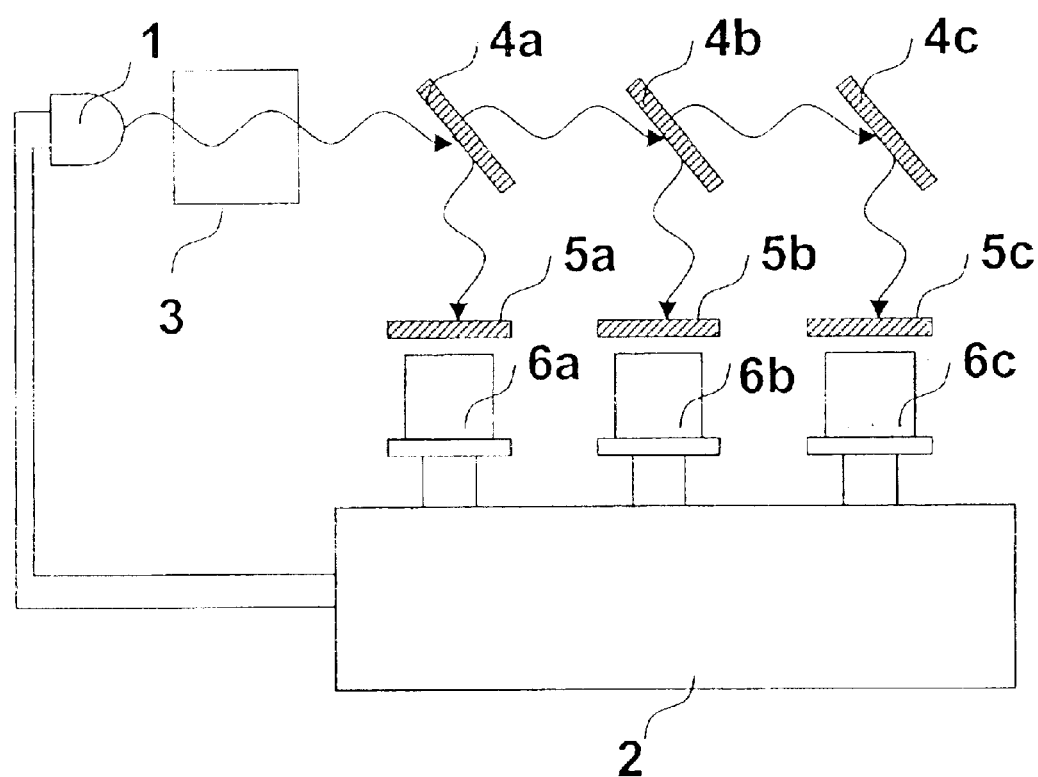
FIG. 1, a schematic illustration of an infrared optical gas measuring instrument with three filters, which can be used for the method of the invention.

In FIG. 1, an infrared optical gas measuring instrument with three filters 5a, 5b, 5c, which can be used for the method of the invention, is shown schematically. The gas measuring instrument includes an infrared optical radiation source 1, which is actuated and controlled via an evaluation and control unit 2. The radiation output by the infrared optical radiation source 1 passes through a radiation-permeable cuvette 3, which contains the gas or gas mixture to be identified and whose partial pressure is to be measured. Next, with the aid of three beam splitters 4a, 4b and 4c, the radiation is carried to three filters 5a, 5b, 5c, each with different transmission wavelength ranges in the range between 3 and 10 micrometers. Downstream of each filter 5a, 5b, 5c is a respective detector 6a, 6b, 6c, which measures the exit intensity of the radiation and transmits the measured value onto the evaluation and control unit 2.

Figure 2:
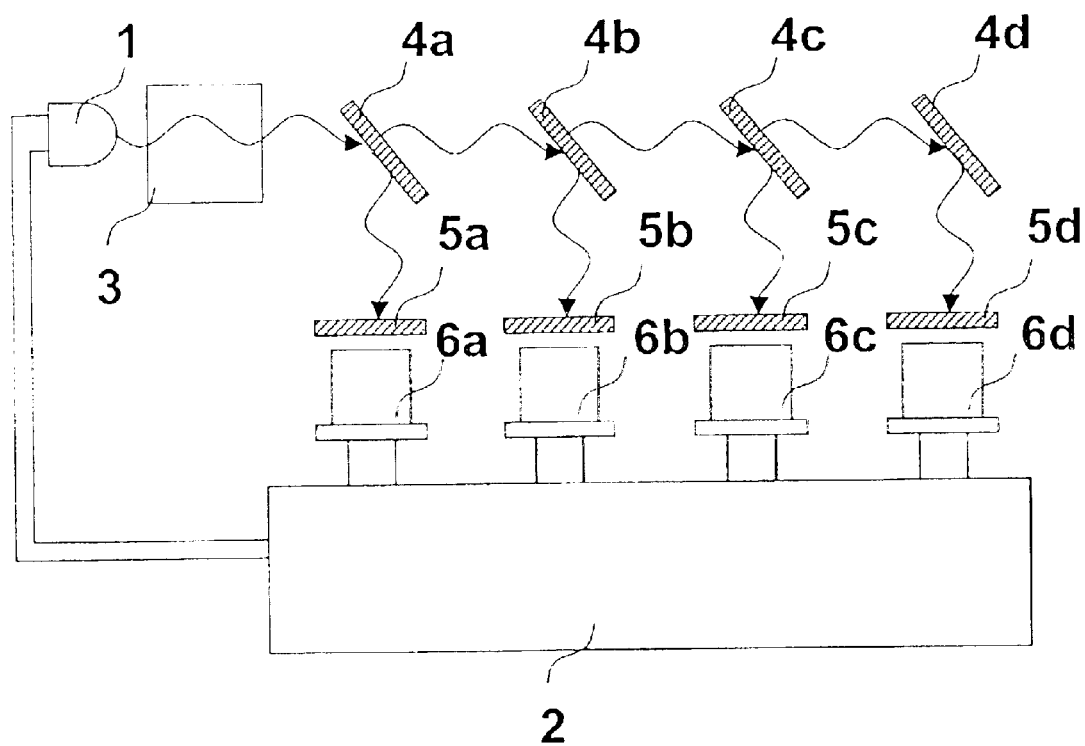
FIG. 2, a schematic illustration of an infrared optical gas measuring instrument with four filters, which can be used for the method of the invention.

In FIG. 2, an infrared optical gas measuring instrument with four filters 5a, 5b, 5c, 5d is shown schematically; it differs from the infrared optical gas measuring instrument of FIG. 1 only in having one additional beam splitter 4d, one additional filter 5d, and one additional detector 6d, which in principle are structurally identical to the beam splitters 4a, 4b, 4c, the filters 5a, 5b, 5c, and the detectors 6a, 6b, 6c.

Figure 3:
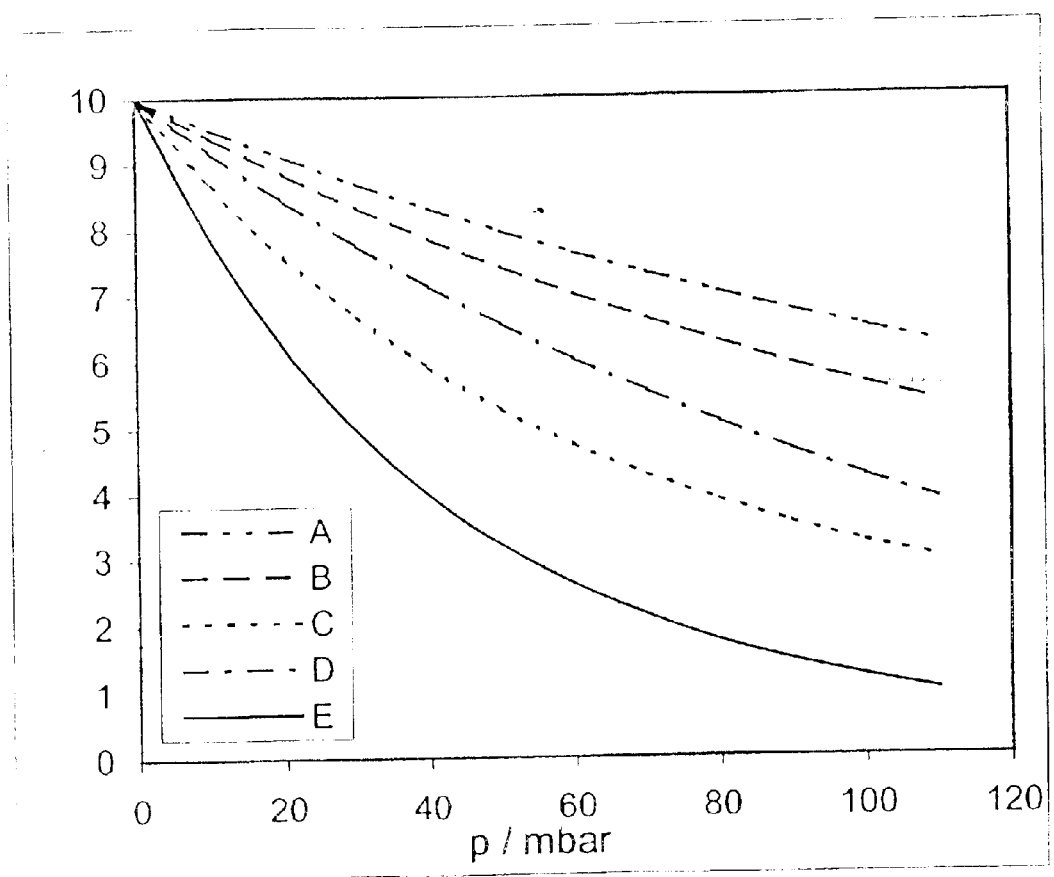
FIG. 3, five calibration curves for five different anesthesia gases A, B, C, D, E and for a first filter with a transmission wavelength range in the range from 3 to 10 micrometers.

In FIG. 3, five different calibration curves for five different anesthesia gases A, B, C, D, E and for the first filter 5a, with a transmission wavelength range in the range from 3 to 10 micrometers, are shown. A stands for halothane, B for enflurane, C for isoflurane, D for sevoflurane, and E for desflurane. On the abscissa, the partial pressure p of each anesthesia gas is plotted in mbar (millibars), and on the ordinate, as a function of this partial pressure, the exit intensity of the infrared optical radiation transmitted through the applicable anesthesia gas, once it has passed through the first filter 5a, is plotted nondimensionally.

Figure 4:
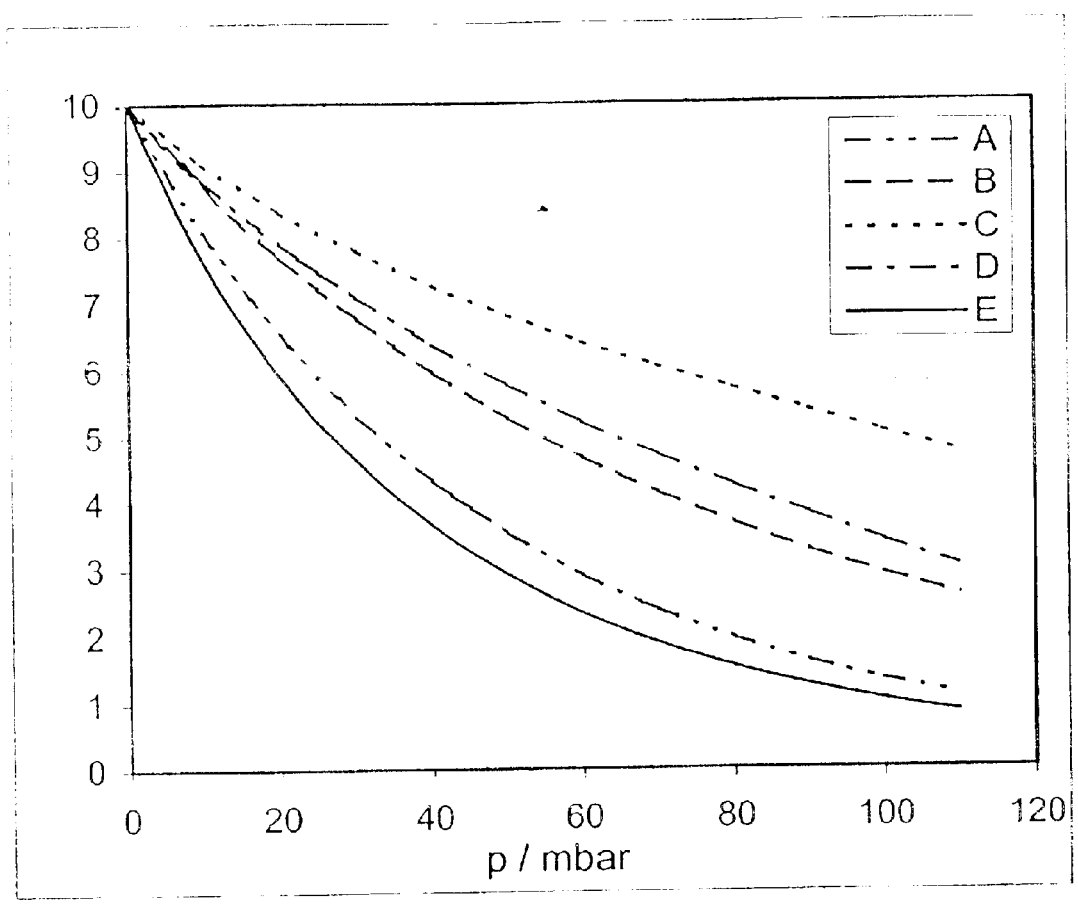
FIG. 4, five calibration curves for the five different anesthesia gases of FIG. 3 and for a second filter, with a transmission wavelength range in the range from 3 to 10 micrometers but different from the first filter.

Corresponding calibration curves are shown in FIG. 4 for the five anesthesia gases A, B, C, D, E and the second filter 5b, with a transmission wavelength range in the range from 3 to 10 micrometers but different from the first filter 5a.

Figure 5:
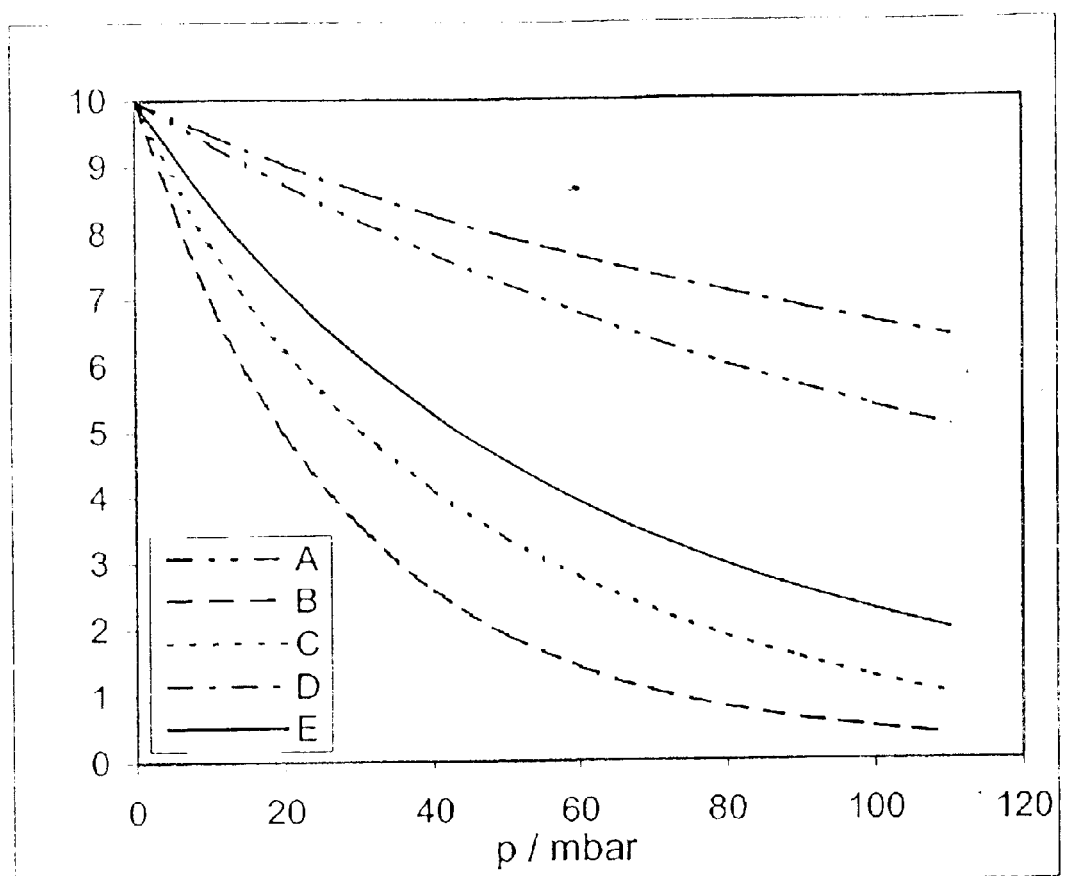
FIG. 5, five calibration curves for the five different anesthesia gases of FIG. 3 and for a third filter, with a transmission wavelength range in the range from 3 to 10 micrometers but different from the first and second filters.

Correspondingly, in FIG. 5, calibration curves for the five anesthesia gases A, B, C, D, E and the third filter 5c, with a transmission wavelength range in the range from 3 to 10 micrometers which differs from the transmission wavelength ranges of the first filter 5a and the second filter 5b, are shown.

In FIGS. 3 through 5, a total of 15 calibration curves are shown, which each plot the exit intensities for each individual gas A, B, C, D, E and each filter 5a, 5b, 5c as a function of the partial pressure.

For an unknown gas mixture and for each of the three filters 5a, 5b, 5c, the exit intensity $S_1$, $S_2$, $S_3$ of the infrared optical radiation transmitted through the gas mixture is measured. The result in this example is $S_1=5$ for the first filter 5a, $S_2=7$ for the second filter 5b, and $S_3=6$ for the third filter 5c.

The table in FIG. 6, for each of the ten mixture pairs, each of which comprises two of the five possible anesthesia gases A, B, C, D, E, shows those pairs of partial pressures that, if the applicable mixture pairs with these partial pressures occur, lead to values $S_1'$, $S_2'$, $S_3'$ for exit intensities, which best correspond to the measured exit intensities $S_1$, $S_2$, $S_3$.

The determination of a pair of partial pressures from the previously generated calibration curves of FIGS. 3 through 5 will now be explained, taken as an example a mixture pair A–B comprising the anesthesia gases A and B:

First, in accordance with Lambert-Beer's law, the exit intensity $S_{AB}$ measured for each filter for the mixture pair A–B is used as the product of the exit intensities $S_A$ and $S_B$ of the individually occurring gases A and B in the mixture pair A–B and is multiplied by a correction factor $K_{AB}$:

$$S_{AB}=S_A \times S_B \times \exp(-k_{AB}).$$

The correction factor $K_{AB}=\exp(-k_{AB})$ depends in each case on the filter 5a, 5b, 5c and its specific transmission wavelength range, and also on the interaction between the molecules of the gases A and B.

The correction factors can be determined beforehand for all the mixture pairs, by calculating the appropriate correction factors for a few partial pressures and then interpolating the other correction factors from them. It is equally conceivable to determine the correction factors experimentally beforehand.

The exit intensities $S_{AB}$, $S_A$, $S_B$ are converted into the extinctions $I_{AB}$, $I_A$, $I_B$; the relation between the exit intensities and the extinctions is expressed by the equations $I_{AB}=-\ln S_{AB}$, $I_A=-\ln S_A$, and $I_B=-\ln S_B$.

The above equation can then be combined as $I_{AB}=I_A+I_B+k_{AB}$.

These conversions are performed for all three filters 5a, 5b, 5c, and what is obtained is the following equation system with the three-dimensional vectors $I_{AB}$, $I_A$, $I_B$ and $k_{AB}$:

$$I_{AB}=I_A+I_B+k_{AB}.$$

The vectors $I_A$ and $I_B$, whose components represent the respective extinctions of the gases A and B at the three different filters, are approximated by means of polynomial functions $P_A=P_A(p_A)$ and $P_B=P_B(p_B)$, so that the equation takes the following form:

$$I_{AB}=P_A(p_A)+P_B(p_B)+k_{AB}.$$

In this example, for the polynomials $P_A(p_A)$ and $P_B(p_B)$, a straight line is selected in each case:

$$P_A(p_A)=m_A \times p_A+a \text{ and } P_B(p_B)=m_B \times p_B+b.$$

The vectors $m_A$ and $m_B$ designate the directions of the straight lines, and the vectors a and b represent location vectors through which the straight lines pass.

The equation then becomes $$I_{AB}=m_A \times p_A+a+m_B \times p_B+b+k_{AB}.$$

Accordingly, a linear equation system exists, with three equations for the two unknown variables $p_A$ and $p_B$; that is, the variables sought, $p_A$ and $p_B$, are overdetermined. With the help of methods known from linear algebra, partial pressures $p_A^*$ and $p_B^*$ are therefore determined such that the deviation between the measured exit intensities and the exit intensities calculated by means of the above equation system is minimal.

The values shown in the table in FIG. 6 have all been determined in the same way as the partial pressures $p_A^*$ and $p_B^*$.

The table in FIG. 7, for each of the ten possible mixture pairs, shows the exit intensities $S_1'$ for the first filter 5a, $S_2'$ for the second filter 5b, and $S_3'$ for the third filter 5c, calculated from the partial pressures of the table in FIG. 6. For calculating the exit intensities $S_1'$, $S_2'$, $S_3'$ from the partial pressures, Lambert-Beer's law is used, always on the precondition that the total pressure is known, and thus the gas concentration is obtained from the quotient of the partial pressure and the total pressure. A product approach is used. This means that the exit intensity for each mixture pair is set as a product of the exit intensities of the gases individually present in the mixture pair.

The table in FIG. 8, for each of the ten possible mixture pairs in column one, shows in columns two through four the distance, that is, the amount of the difference, between the calculated exit intensity $S_1'$, $S_2'$, $S_3'$ and the actually measured exit intensity $S_1$, $S_2$, $S_3$ at the applicable filter 5a, 5b, 5c. In the fifth column, for each mixture pair, the sum of the distances, that is, the amounts of the differences, from columns two through four is calculated, and in the sixth column, for each mixture pair, the sum of the squares of the distances from columns two through four is calculated. In this way, a distance measure is specified in the fifth and sixth columns, in accordance with which distance measure it is assessed which of the ten possible mixture pairs is identified as the unknown gas mixture, and which two associated partial pressures will be used. In the present example, the mixture pair B-D with partial pressures $p_B=12.22$ and $p_D=18.55$ best matches the actually measured exit intensities $S_1$, $S_2$, $S_3$ both for the distance measure using the sum of distances $\Sigma\ 1 \leq i \leq 3\ |S_i-S_i'|=0.21$, and the distance measure using the sum of distances of squares $\Sigma\ 1 \leq i \leq 3\ (S_i-S_i')^2=0.004$.

What is claimed is:

1. A method for identification and partial-pressure determination of two gases in an unknown gas mixture comprising n possible gases by measuring the infrared optical radiation emitted by a radiation source and transmitted through a cuvette holding the unknown gas mixture, which radiation passes through m filters with different transmission wavelength ranges, which are followed downstream by at least one detector for measuring and transmitting the exit intensities of the radiation onward to an evaluation and control unit, wherein n is a number greater than 2, and m is a number less than n, comprising the following steps:

a) for each of the n gases and each of the m filters, a calibration curve describing the dependency of the exit intensity of the infrared optical radiation, which radiation is transmitted through the gas and has passed through the filter, on the partial pressure of the gas is first ascertained;

b) for the unknown gas mixture and each of the m filters, the exit intensity of the infrared optical radiation, transmitted through the gas mixture, that has passed through the filter is measured by the at least one downstream detector and transmitted on to the evaluation and control unit;

c) for each of the possible pairs of mixtures that each comprise two of the n possible gases, by means of the evaluation and control unit from the exit intensities ascertained in step a), the pair of partial pressures whose associated exit intensities best correspond to the exit intensities measured in step b) in accordance with a distance measure specified in the evaluation and control unit, is determined;

d) the two gases of the gas mixture having the pair, determined in step c), of partial pressures whose associated exit intensities best correspond to the measured exit intensities in accordance with the specified distance dimension, are identified by the evaluation and control unit as gases of the unknown gas mixture.

2. The method of claim 1, wherein the unknown gas mixture comprises n=5 possible gases.

3. The method of claim 2, wherein the n=5 gases involve the five anesthesia gases in the group comprising halothane, enflurane, isoflurane, sevoflurane, and desflurane.

4. The method of claim 2, wherein the infrared optical radiation passes through m=3 filters.

5. The method of claim 2, wherein the infrared optical radiation passes through m=4 filters.

6. The method of claim 3, wherein the infrared optical radiation passes through m=3 filters.

7. The method of claim 3, wherein the infrared optical radiation passes through m=4 filters.

8. The method of claim 1, wherein the specified distance measure is the sum of the distances between the m exit intensities of one of the mixture pairs, for a particular pair of partial pressures, and the m measured exit intensities of the unknown gas mixture.

9. The method of claim 1, wherein the specified distance measure is the sum of the squares of the distances between the m exit intensities of one of the mixture pairs, for a particular pair of partial pressures, and the m measured exit intensities of the unknown gas mixture.

* * * * *